United States Patent [19]

Merz

[11] Patent Number: 4,914,095

[45] Date of Patent: Apr. 3, 1990

[54] USE OF IMIDAZOBENZODIAZEPINES FOR PSYCHOTIC DISORDERS

[75] Inventor: Walter Merz, Basel, Switzerland

[73] Assignee: Hoffmann-La Roche Inc., Nutley, N.J.

[21] Appl. No.: 297,228

[22] Filed: Jan. 13, 1989

[30] Foreign Application Priority Data

Jan. 15, 1988 [CH] Switzerland ............................ 143/88

[51] Int. Cl.$^4$ .............................................. A61K 31/54
[52] U.S. Cl. ................................................... 514/219
[58] Field of Search ......................................... 514/219

[56] References Cited

U.S. PATENT DOCUMENTS 4,352,815 10/1982 Hunkeler et al. .................... 514/219

Primary Examiner—Stanley J. Friedman

Attorney, Agent, or Firm—Jon S. Saxe; Bernard S. Leon

[57] ABSTRACT

A compound of the formula

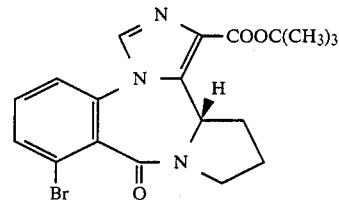

is useful to treat psychotic disorders in humans, especially schizophrenia, and to prevent exacerbations thereof. The compound can be used as a single therapeutic agent or in combination with neuroleptics such as haloperidol.

5 Claims, No Drawings

USE OF IMIDAZOBENZODIAZEPINES FOR PSYCHOTIC DISORDERS

SUMMARY OF THE INVENTION

The present invention comprises the use of t-butyl (S)-8-bromo-11,12,13,13a-tetrahydro-9-oxo-9H-imidazo[1.5-a]pyrrolo[2,1-c][1,4]benzodiazepine-1-carboxylate, having the formula

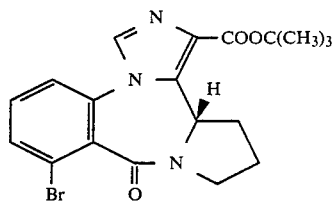

which for convenience sake is referred to hereinafter as "Coupound A", to treat psychotic disorders in humans, especially schizophrenia, and to prevent exacerbations thereof. For these purposes Compound A can be used as a single therapeutic agent or in combination with neuroleptics such as haloperidol.

Also included within the scope of the present invention are pharmaceutical compositions containing effective amounts of Compound A together with an inert pharmaceutical carrier.

DETAILED DESCRIPTION OF THE INVENTION

Compound A per se is a known substance, and its preparation and anticonvulsive and anxiolytic properties are described, for example, in European Patent Publication No. 59 391.

The following description of schizophrenia conforms to the diagnostic criteria of the third revised edition of the American Statistical and Diagnostic Handbook (Diagnostic and Statistical Manual of Mental Disorders, DSM-III-R) of the Americal Psychiatric Association (APA). Schizophrenia is a psychopathic disorder of unknown origin, which usually appears for the first time in early adulthood and is marked by a number of characteristics, psychotic symptoms, progression, phasic development and deterioration in social behavior and professional capability in the region below the highest level ever attained. Characteristic psychotic symptoms are disorders of thought content (multiple, fragmentary, incoherent, implausible or simply delusional contents or ideas of persecution) and of mentality (loss of association, flight of imagination, incoherence up to incomprehensibility), as well as disorders of perceptibility (hallucinations), of emotions (superficial or inadequte emotions), of self-perception, of intentions and impulses, of interhuman relationships, and finally psychomotoric disorders (such as catatonia). A large number of other symptoms are also assoicated with this disorder.

A difference exists between the prodromal, active and residual phases. Subchronic schizophrenia, subchronic schizophrenia with acute exacerbation, chronic schizophrenia and chronic schizophrenia with acute exacerbation are differentiated according to the number and type of phases. Finally, a catatonic, a disorganized-hebephrenic and a paranoid type of schizophrenia, as well as mixed forms of the various tupes, are differentiated according to prevalent psychotic symptoms.

The current, symptomatic therapy of schizophrenia and of similar psychotic disorders such as paranoia, schizo-emotional psychoses, schizophreniform psychosis and other psychoses is pharmacotherapy using neuroleptics. Disadvantages of neuroleptics include the large number—to some extent irreversible—of side effects such as Parkinsonism, secondary dyskinesia, prolactin increase and its consequences and anticholinergic side effects. Moreover, current therapies generally have an inadequate or unfavorable effect on disorders of the emotions, of impulses, of intentions and of psychomotoric disorders ("negative" symptoms of schizophrenia, in contrast to the so-called "productive" symptoms such as, for example, hallucinations or delusional ideas).

Benzodiazepines in high dosages have been investigated from time to time for their antipsychotic effects in schizophrenia. Where the effect was not limited at the outset to the inherent anxiolytic effect, high-dosage benzodiazepine therapy had to be withdrawn after a short time because either intolerable side effects appeared or the therapy moved into an experimental dosage range which was not permitted according to governmental regulations.

It has now been surprisingly discovered that Compound A has, in addition to the known anticonvulsive and anxiolytic activities, a pronounced antipsychotic activity not only against productive symptoms but also against negative symptoms. Further, the use of Compound A for this purpose is characterized by very good tolerability, especially the absence of extrapyramidal motoric, anticholinergic and prolactin-induced side effects.

The effect of Compound A on schizophrenia in a single blind study on 10 patients with chronic paranoid schizophrenia is shown in the following evaluation.

Compound A was used in this study in the form of tablets containing 0.5 mg of active substance.

The patients, which had been selected according to the criteria of DSM-III, received during 4 weeks a divided dosage of at least 1.5 mg daily. During the first week of treatment this daily dosage could be titrated up to 4.5 mg according to activity and side effects. The optimal dosage was maintained during the second and third weeks and was reduced stepwise to zero during the fourth week of treatment. The treatment was concluded by the fifth week, during which a placebo was administered. Investigation days were 0, 1, 3, 7, 14, 21, 28, 30 and 35, respectively. On all of these days of treatment the data were ascertained according to the Brief Psychiatric Rating Scale (BPRS; an index of psychotic symptoms), the anxiety scale according to Covi and the depression scale according to Raskin, Clinical Global Impressions (CGI), as well as the vital functions and an index of the side effects. Hematological and clinical-chemical parameters were ascertained before the beginning of the treatment with Compound A and after the conclusion of such treatment, combined with an ECG and a general medical examination. The serum levels of prolactin were measured on days 0, 7, 14 and 21 and the extra-pyramidal side effects were ascertained on the basis of the scale of Simpson and Angus.

Nine males and one female with a acute exacerbation of chronic schizophrenia were included in the study. Their average age was 33±4.9 years, their average body weight was 68±7.3 kg and their average height was 172±4.8 cm. At the time of introduction into the study the disorder had lasted, on average, 79±66 months and the patients had been hospitalized, on average, 5.7±3.3 times. The occurrence of the disorder was evaluated in most of the patients as "severe", a fact which is also underlined by the initial score of 65 points in the BPRS.

All patients, except one, reacted very well to the treatment with Compound A and better than to the previous treatment with neuroleptics (in most cases, haloperidol was used previously). The number and intensity not only of the productive but also of the negative psychotic symptoms clearly decreased from the third day of the treatment. This improvement in the clinical condition could be seen well on the BPRS: before the beginning of treatment the average total score was 65.5 points, after treatment for one day 60.8, after 3 days 37.4, after 7 days 13.3, after 14 days 9.5, after 21 days 7.1, and after treatment for 28 days, at the end of the exclusion phase, 5.8 points. With the use of the placebo during the 5th week of treatment, a slight increase was again noted (day 30: 7.4 points; day 35: 11.2 points). The same profile appeared in the CGI: severity of the disorder (maximum 6, minimum 0 points); before treatment 4.9 points; day 1, 4.6; day 3, 3,3; day 7, 1.8; day 14, 1.4; day 21, 1.2; day 28, 1.1; with futher increase to 1.2 on day 35; therapeutic effect (maximum 3, minimum 0 points): day 1, 0.6 points; day 3, 2.2; day 7, 2.7; day 14, 2.8; days 21 and 28, 2.9 points. An improvement occurred in all symptoms and factors of the BPRS, not only in symptoms of anxiety and depression. The improvement in the functional and social behavior of the patients was shown not only by the psychiatric scales, but was also evident from the observable behavior of the patients themselves. The improvement persisted beyond the end of the treatment with Compound A, since the values after placebo treatment for 7 days (day 35) were only insignificantly higher than for the 7 previous days.

The very good overall tolerability of Compound A can be seen on the basis of the side effects concerning CGI (worst value 3, best value 0 points) as follows: after treatment for one day the value was 0.1 points; after 3 days 0.1, after 7 days 0.0; after 14 days 0.2 and after 21 and 28 days in each case 0.0 points. The scale according to Simpson and Angus shows simply the disappearance of the extrapyramidal disorders induced by the previous neuroleptic treatment as follows: 1.1 points on day 1; 1.1 on day 3; 0.6 on days 7 and 14 and 0.4 points on day 28. The serum prolactin level (normal value <20 ng/ml) shows behavior as follows: 21.5±19.8 on day 0; 10.2±8.3 on day 7; 5.7±2.2 on day 14 and 6.7±2.7 ng/ml on day 21.

The results of this study prove that Compound A has an antipsychotic activity against paranoid schizophrenia, with simultaneous outstanding tolerance. Further, no extra-pyramidal and prolactin-induced side effects were observed.

In the practice of the present invention Compound A is preferably used in the form of perorally administrable pharmaceutical preparations, such as in the form of tablets, coated tablets, dragees, hard and soft gelatine capsules, solutions, emulsions or suspensions. Tablets are preferred as the dosage form.

For the preparation of pharmaceutical preparations Compound A is processed with pharmaceutically inert, inorganic or organic carriers. As such carriers for tablets, coated tablets, dragees and hard gelatine capsules there can be used, for example, lactose, maize starch or derivatives thereof, talc, stearic acid or its salts and the like. Suitable carriers for soft gelatine capsules are, for example, vegetable oils, waxes, fats, semi-solid and liquid polyols and the like. Suitable carriers for the preparation of solutions and syrups are, for example, water, polyols, saccharose, invert sugar, glucose and the like.

The pharmaceutical preparations can contain, in addition, preserving agents, solubilizing agents, stabilizing agents, wetting agents, emulsifying agents, sweetening agents, coloring agents, flavoring agents, salts for varying the osmotic pressure, buffers, coating agents or antioxidants. They can also contain other therapeutically useful substances, for example, the neuroleptics already mentioned.

As mentioned earilier, Compound A can be used in the treatment of psychotic disorders, especially schizophrenia, and for the prevention of exacerbations thereof. The dosage can vary according to the severity of the disorder, age and weight of the patient and is, of course, adjustable according to the individual requirements in each particular case. In general, in the case of oral administration a daily dosage of about 0.5 mg to 6 mg should be appropriate.

The following Example describes a suitable dosage form for the practical application of the present invention. However, it is not intended to limit its scope in any manner.

EXAMPLE

| Ingredients | Per Tablet |
|---|---|
| Compound A | 0.5 mg |
| Lactose | 126.5 mg |
| Maize starch | 54.0 mg |
| Povidone K30 | 8.0 mg |
| Na carboxymethylstarch | 10.0 mg |
| Magnesium stearate | 1.0 mg |
| Total: | 200.0 mg |

Compound A, the lactose and the maize starch are mixed and granulated with an aqueous and/or alcoholic solution of Povidone. The dried and crushed granulate is mixed with Na carboxymethylstarch and magnesium stearate and subsequently pressed into tablets of 200 mg each.

I claim:

1. A method of treating or preventing psychotic disorders comprising administering to a host having such a disorder an antipsychotic amount of a compound of the formula

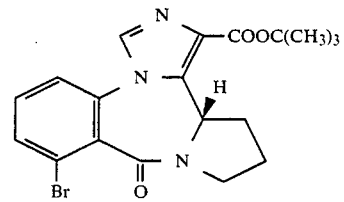

2. A method according to claim 1, in which the psychotic disorder is schizophrenia.

3. A method according to claim 1 in which the compound is administered orally.

4. A method according to claim 3 in which the oral administration comprises the use of a tablet containing the compound.

5. A method according to claim 3 in which a daily dosage of from about 0.5 mg to 6 mg is administered.

* * * * *